United States Patent
Yang

(10) Patent No.: US 6,228,609 B1
(45) Date of Patent: May 8, 2001

(54) SOLUBLE FLK-2 SEQUENCE

(75) Inventor: Zhi Yang, Palo Alto, CA (US)

(73) Assignee: SyStemix, Inc., DE (US)

( * ) Notice: Subject to any disclaimer, the term of this patent is extended or adjusted under 35 U.S.C. 154(b) by 0 days.

(21) Appl. No.: 07/912,122

(22) Filed: Jul. 9, 1992

(51) Int. Cl.[7] .................. C12P 21/06; C12N 15/00; C12N 15/09; C07H 21/04
(52) U.S. Cl. ................ 435/69.1; 435/172.1; 435/320.1; 536/23.5
(58) Field of Search .................. 435/69.1, 172.1, 435/320.1; 536/23.5; 935/10; 514/12; 530/387.1, 350

(56) References Cited

U.S. PATENT DOCUMENTS 5,185,438 * 2/1993 Lemischka ..................... 536/23.2

OTHER PUBLICATIONS

O. Rosnet et al. Oncogene 6:1641–50 1991.*
O. Rosnet et al. Genomics 9:380–85 1991.*
W. Matthews, et al. (1991) Cell 65:1143–1152. A receptor tyrosine kinase specific to hematopoietic stem and progenitor cell–enriched populations.

W. Matthews, et al. (1991) P.N.A.S. 88:9026–9030. A receptor tyrosine kinase cDNA isolated from a population of enriched primitive hematopoietic cells and exhibiting close genetic linkage to c–kit.

C. Jordan, et al. (1990) Cell 61:953–963. Cellular and developmental properties of fetal hematopoietic stem cells.

C. Jordan and I. Lemischka (1990) Genes & Development 4:220–232. Clonal and systemic analysis of long–term hematopoiesis in the mouse.

* cited by examiner

Primary Examiner—Gary L. Kunz
Assistant Examiner—Robert S. Landsman
(74) Attorney, Agent, or Firm—Geoffrey M. Karny

(57) ABSTRACT

A purified soluble form of Flk-2 is provided, as the DNA sequence and as the protein. In addition, a partial DNA sequence of the human Flk-2 is also provided. The proteins find use in modulating hematopoiesis in culture and in vivo, as well as for the production of antibodies for assays of the proteins.

5 Claims, No Drawings

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:1:

GAGGCCTGGC TACCGCGCGC TCCG                                          24

(2) INFORMATION FOR SEQ ID NO:2:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:2:

ATGGATGGAA ATAAACTTTC TACTGTA                                       27

(2) INFORMATION FOR SEQ ID NO:3:

(i) SEQUENCE CHARACTERISTICS:
        (A) LENGTH: 1894 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 31..1473

(xi) SEQUENCE DESCRIPTION: SEQ ID NO:3:

GCGGCCTGGC TACCGCGCGC TCCGGAGGCC ATG CGG GCC TTG GCG CAG CGC AGC      54
                                Met Arg Ala Leu Ala Gln Arg Ser
                                  1               5

GAC CGG CGG CTG CTG CTG CTT GTT GTT TTG TCA GTA ATG ATT CTT GAG      102
Asp Arg Arg Leu Leu Leu Leu Val Val Leu Ser Val Met Ile Leu Glu
         10                  15                  20

ACC GTT ACA AAC CAA GAC CTG CCT GTG ATC AAG TGT GTT TTA ATC AGT      150
Thr Val Thr Asn Gln Asp Leu Pro Val Ile Lys Cys Val Leu Ile Ser
 25                  30                  35                  40

CAT GAG AAC AAT GGC TCA TCA GCG GGA AAG CCA TCA TCG TAC CGA ATG      198
His Glu Asn Asn Gly Ser Ser Ala Gly Lys Pro Ser Ser Tyr Arg Met
                 45                  50                  55

GTG CGA GGA TCC CCA GAA GAC CTC CAG TGT ACC CCG AGG CGC AGT AGT      246
Val Arg Gly Ser Pro Glu Asp Leu Gln Cys Thr Pro Arg Arg Gln Ser
             60                  65                  70

```
GAA GGG ACG GTA TAT GAA GCG GCC ACC GTG GAG GTG GCC GAG TCT GGG      294
Glu Gly Thr Val Tyr Glu Ala Ala Thr Val Glu Val Ala Glu Ser Gly
        75                  80                  85

TCC ATC ACC CTG CAA GTG CAG CTC GCC ACC CCA GGG GAC CTT TCC TGC      342
Ser Ile Thr Leu Gln Val Gln Leu Ala Thr Pro Gly Asp Leu Ser Cys
    90                  95                  100

CTC TGG GTC TTT AAG CAC AGC TCC CTG GGC TGC CAG CCG CAC TTT GAT      390
Leu Trp Val Phe Lys His Ser Ser Leu Gly Cys Gln Pro His Phe Asp
105                 110                 115                 120

TTA CAA AAC AGA GGA ATC GTT TCC ATG GCC ATC TTG AAC GTG ACA GAG      438
Leu Gln Asn Arg Gly Ile Val Ser Met Ala Ile Leu Asn Val Thr Glu
            125                 130                 135

ACC CAG GCA GGA GAA TAC CTA CTC CAT ATT CAG AGC GAA CGC GCC AAC      486
Thr Gln Ala Gly Glu Tyr Leu Leu His Ile Gln Ser Glu Arg Ala Asn
        140                 145                 150

TAC ACA GTA CTG TTC ACA GTG AAT GTA AGA GAT ACA CAG CTG TAT GTG      534
Tyr Thr Val Leu Phe Thr Val Asn Val Arg Asp Thr Gln Leu Tyr Val
    155                 160                 165

CTA AGG AGA CCT TAC TTT AGG AAG ATG GAA AAC CAG GAT GCA CTG CTC      582
Leu Arg Arg Pro Tyr Phe Arg Lys Met Glu Asn Gln Asp Ala Leu Leu
170                 175                 180

TGC ATC TCC GAG GGT GTT CCG GAG CCC ACT GTG GAG TGG GTG CTC TGC      630
Cys Ile Ser Glu Gly Val Pro Glu Pro Thr Val Glu Trp Val Leu Cys
185                 190                 195                 200

AGC TCC CAC AGG GAA AGC TGT AAA GAA GAA GGC CCT GCT GTT GTC AGA      678
Ser Ser His Arg Glu Ser Cys Lys Glu Glu Gly Pro Ala Val Val Arg
            205                 210                 215

AAG GAG GAA AAG GCA CAT TCA AAT TCC AGC ATG CCT GGT TCA CGA GAA      726
Lys Glu Glu Lys Ala His Ser Asn Ser Ser Met Pro Gly Ser Arg Glu
        220                 225                 230

GTT CAG TTA CAC CCG CCC TTG GAT CAG CTC TCA GGG TTC AAT GGG AAT      774
Val Gln Leu His Pro Pro Leu Asp Gln Leu Ser Gly Phe Asn Gly Asn
    235                 240                 245

TCA ATT CAT TCT GAA GAT GAG ATT GAA TAT GAA AAC CAG AAG AGG CTG      822
Ser Ile His Ser Glu Asp Glu Ile Glu Tyr Glu Asn Gln Lys Arg Leu
    250                 255                 260

GCA GAA GAA GAG GAG GAA GAT TTG AAC GTG CTG ACG TTT GAA GAC CTC      870
Ala Glu Glu Glu Glu Glu Asp Leu Asn Val Leu Thr Phe Glu Asp Leu
265                 270                 275                 280

CTT TGC TTT GCG TAC CAA GTG GCC AAA GGC ATG GAA TTC CTG GAG TTC      918
Leu Cys Phe Ala Tyr Gln Val Ala Lys Gly Met Glu Phe Leu Glu Phe
            285                 290                 295

AAG TCG TGT GTC CAC AGA GAC CTG GCA GCC AGG AAT GTG TTG GTC ACC      966
Lys Ser Cys Val His Arg Asp Leu Ala Ala Arg Asn Val Leu Val Thr
        300                 305                 310

CAC GGG AAG GTG GTG AAG ATC TGT GAC TTT GGA CTG GCC CGA GAC ATC     1014
His Gly Lys Val Val Lys Ile Cys Asp Phe Gly Leu Ala Arg Asp Ile
    315                 320                 325

CTG AGC GAC TCC AGC TAC GTC GTC AGG GGC AAC GCA CGG CTG CCG GTG     1062
Leu Ser Asp Ser Ser Tyr Val Val Arg Gly Asn Ala Arg Leu Pro Val
330                 335                 340

AAG TGG ATG GCA CCC GAG AGC TTA TTT GAA GGG ATC TAC ACA ATC AAG     1110
Lys Trp Met Ala Pro Glu Ser Leu Phe Glu Gly Ile Tyr Thr Ile Lys
345                 350                 355                 360

AGT GAC GTC TGG TCC TAC GGC ATC CTT CTC TGG GAG ATA TTT TCA CTG     1158
Ser Asp Val Trp Ser Tyr Gly Ile Leu Leu Trp Glu Ile Phe Ser Leu
            365                 370                 375

GGT GTG AAC CCT TAC CCT GGC ATT CCT GTC GAC GCT AAC TTC TAT AAA     1206
Gly Val Asn Pro Tyr Pro Gly Ile Pro Val Asp Ala Asn Phe Tyr Lys
```

-continued

```
                380                 385                 390
CTG ATT CAG AGT GGA TTT AAA ATG GAG CAG CCA TTC TAT GCC ACA GAA      1254
Leu Ile Gln Ser Gly Phe Lys Met Glu Gln Pro Phe Tyr Ala Thr Glu
        395                 400                 405

GGG ATA TAC TTT GTA ATG CAA TCC TGC TGG GCT TTT GAC TCA AGG AAG      1302
Gly Ile Tyr Phe Val Met Gln Ser Cys Trp Ala Phe Asp Ser Arg Lys
410                 415                 420

CGG CCA TCC TTC CCC AAC CTG ACT TCA TTT TTA GGA TGT CAG CTG GCA      1350
Arg Pro Ser Phe Pro Asn Leu Thr Ser Phe Leu Gly Cys Gln Leu Ala
425                 430                 435                 440

GAG GCA GAA GAA GCA TGT ATC AGA ACA TCC ATC CAT CTA CCA AAA CAG      1398
Glu Ala Glu Glu Ala Cys Ile Arg Thr Ser Ile His Leu Pro Lys Gln
                445                 450                 455

GCG GCC CCT CAG CAG AGA GGC GGG CTC AGA GCC CAG TCG CCA CAG CGC      1446
Ala Ala Pro Gln Gln Arg Gly Gly Leu Arg Ala Gln Ser Pro Gln Arg
                460                 465                 470

CAG GTG AAG ATT CAC AGA GAA AGA AGT TAGCGAGGAG GCCTTGGACC            1493
Gln Val Lys Ile His Arg Glu Arg Ser
        475                 480

CCGCCACCCT AGCAGGCTGT AGACCGCAGA GCCAAGATTA GCCTCGCCTC TGAGGAAGCG    1553

CCCTACAGCG CGTTGCTTCG CTGGACTTTT CTCTAGATGC TGTCTGCCAT TACTCCAAAG    1613

TGACTTCTAT AAAATCAAAC CTCTCCTCGC ACAGGCGGGA GAGCCAATAA TGAGACTTGT    1673

TGGTGAGCCC GCCTACCCTG GGGGCCTTTC CACGAGCTTG AGGGGAAAGC CATGTATCTG    1733

AAATATAGTA TATTCTTGTA AATACGTGAA ACAAACCAAA CCCGTTTTTT GCTAAGGGAA    1793

AGCTAAATAT GATTTTTAAA AATCTATGTT TTAAAATACT ATGTAACTTT TTCATCTATT    1853

TAGTGATATA TTTTATGGAT GGAAATAAAC TTTCTACTGT A                       1894

(2) INFORMATION FOR SEQ ID NO:4:

(i) SEQUENCE CHARACTERISTICS:
        (A) LENGTH: 481 amino acids
        (B) TYPE: amino acid
        (D) TOPOLOGY: linear (ii) MOLECULE TYPE: protein (xi) SEQUENCE DESCRIPTION: SEQ ID NO:4:

Met Arg Ala Leu Ala Gln Arg Ser Asp Arg Arg Leu Leu Leu Leu Val
  1               5                  10                  15

Val Leu Ser Val Met Ile Leu Glu Thr Val Thr Asn Gln Asp Leu Pro
                 20                  25                  30

Val Ile Lys Cys Val Leu Ile Ser His Glu Asn Asn Gly Ser Ser Ala
             35                  40                  45

Gly Lys Pro Ser Ser Tyr Arg Met Val Arg Gly Ser Pro Glu Asp Leu
         50                  55                  60

Gln Cys Thr Pro Arg Arg Gln Ser Glu Gly Thr Val Tyr Glu Ala Ala
 65                  70                  75                  80

Thr Val Glu Val Ala Glu Ser Gly Ser Ile Thr Leu Gln Val Gln Leu
                 85                  90                  95

Ala Thr Pro Gly Asp Leu Ser Cys Leu Trp Val Phe Lys His Ser Ser
            100                 105                 110

Leu Gly Cys Gln Pro His Phe Asp Leu Gln Asn Arg Gly Ile Val Ser
        115                 120                 125

Met Ala Ile Leu Asn Val Thr Glu Thr Gln Ala Gly Glu Tyr Leu Leu
    130                 135                 140
```

```
His Ile Gln Ser Glu Arg Ala Asn Tyr Thr Val Leu Phe Thr Val Asn
145                 150                 155                 160

Val Arg Asp Thr Gln Leu Tyr Val Leu Arg Arg Pro Tyr Phe Arg Lys
                165                 170                 175

Met Glu Asn Gln Asp Ala Leu Leu Cys Ile Ser Glu Gly Val Pro Glu
            180                 185                 190

Pro Thr Val Glu Trp Val Leu Cys Ser Ser His Arg Glu Ser Cys Lys
        195                 200                 205

Glu Glu Gly Pro Ala Val Val Arg Lys Glu Lys Ala His Ser Asn
210                 215                 220

Ser Ser Met Pro Gly Ser Arg Glu Val Gln Leu His Pro Pro Leu Asp
225                 230                 235                 240

Gln Leu Ser Gly Phe Asn Gly Asn Ser Ile His Ser Glu Asp Glu Ile
                245                 250                 255

Glu Tyr Glu Asn Gln Lys Arg Leu Ala Glu Glu Glu Glu Asp Leu
            260                 265                 270

Asn Val Leu Thr Phe Glu Asp Leu Leu Cys Phe Ala Tyr Gln Val Ala
        275                 280                 285

Lys Gly Met Glu Phe Leu Glu Phe Lys Ser Cys Val His Arg Asp Leu
290                 295                 300

Ala Ala Arg Asn Val Leu Val Thr His Gly Lys Val Val Lys Ile Cys
305                 310                 315                 320

Asp Phe Gly Leu Ala Arg Asp Ile Leu Ser Asp Ser Ser Tyr Val Val
                325                 330                 335

Arg Gly Asn Ala Arg Leu Pro Val Lys Trp Met Ala Pro Glu Ser Leu
            340                 345                 350

Phe Glu Gly Ile Tyr Thr Ile Lys Ser Asp Val Trp Ser Tyr Gly Ile
        355                 360                 365

Leu Leu Trp Glu Ile Phe Ser Leu Gly Val Asn Pro Tyr Pro Gly Ile
370                 375                 380

Pro Val Asp Ala Asn Phe Tyr Lys Leu Ile Gln Ser Gly Phe Lys Met
385                 390                 395                 400

Glu Gln Pro Phe Tyr Ala Thr Glu Gly Ile Tyr Phe Val Met Gln Ser
                405                 410                 415

Cys Trp Ala Phe Asp Ser Arg Lys Arg Pro Ser Phe Pro Asn Leu Thr
            420                 425                 430

Ser Phe Leu Gly Cys Gln Leu Ala Glu Ala Glu Ala Cys Ile Arg
        435                 440                 445

Thr Ser Ile His Leu Pro Lys Gln Ala Ala Pro Gln Gln Arg Gly Gly
450                 455                 460

Leu Arg Ala Gln Ser Pro Gln Arg Gln Val Lys Ile His Arg Glu Arg
465                 470                 475                 480

Ser (2) INFORMATION FOR SEQ ID NO:5:

(i) SEQUENCE CHARACTERISTICS:
        (A) LENGTH: 146 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

AATAAAAAGG CTAACAGAAA AGTGTTTGGC CAGTGGGTGT CGAGCAGTAC TCTAAATATG      60
```

```
AGTGAGGCCG GGAAAGGGCT TCTGGTCAAA TGCTGTGCGT ACAATTCTAT GGGCACGTCT        120

TGCGAAACCA TCTTTTTAAA CTCACC                                            146

(2) INFORMATION FOR SEQ ID NO:6:

(i) SEQUENCE CHARACTERISTICS:
        (A) LENGTH: 151 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

CTGGAATAGA AAGGCTAACA GAAAAGTGTT TGGACAGTGG GTGTCGAGCA GTACTCTAAA         60

CATGAGTGAA GCCATAAAAG GGTTCTGGTC AAGTGCTGTG ACTACAATTC CCTTGGCACA        120

TCTGTGAGAG CATCCTTTTA AACTCTACCG G                                      151
```

SOLUBLE FLK-2 SEQUENCE

TECHNICAL FIELD

The field of this invention is the identification and use of hematopoietic factor receptors.

BACKGROUND

The process for the development of hematopoietic cells from a self-regenerating stem cell to the mature multi-lineage cells has been the subject of intense investigation. How the host is able to direct a single cell into the multiplicity of pathways which provide such varied cells as lymphocytes, monocytes, macrophages, megakaryocytes and osteoclasts, which is not a complete list, still remains to be elucidated. However, substantial strides have been made in identifying various intermediate cells associated with the different lineages and identifying factors which appear to direct, either by themselves or in combination with other factors, the cells to mature to a particular cell type. For the most part, the factors have been associated with progenitors which are committed to a particular lineage, where the factors result in maturation of the progenitor. Less is known about the factors which direct a totipotent or multipotent cell to be directed to one among many possible lineages.

In order to understand the processes of differentiation and maturation, it will be necessary to know which surface membrane proteins act as receptors for transduction of signals, whether they have soluble forms, the role of soluble forms, and which ligands are associated with the surface membrane proteins. It is therefore of substantial interest to be able to identify ligands, receptors and their soluble forms associated with cell regeneration, proliferation, differentiation, and maturation.

Relevant Literature

Jordan et al. (1990) Cell 81, 953–963 and Matthews et al. (1991) Cell 65, 1143–1152 describe isolation of fetal liver stem cells and molecular cloning of FLK-2, a putative stem cell growth factor receptor. Jordan and Lemischka (1990) *Genes and Development* 4, 220–232 describe a clonal and systemic analysis of long-term hematopoiesis in the mouse.

SUMMARY OF THE INVENTION

A soluble form of FLK-2 molecule (SEQ ID NO:3 and SEQ ID NO:4) is provided where the soluble form lacks the transmembrane sequence as well as portions of the extra-cellular and intra-cellular sequences. In addition, a partial nucleic acid sequence (SEQ ID NO:5) of the gene for human FLK-2 is provided.

DESCRIPTION OF THE SPECIFIC EMBODIMENTS

Methods and compositions are provided associated with the mammalian regulation of hematopoiesis. Particularly, a soluble form of the mammalian fetal liver kinase-2 (FLK-2) is provided, as well as the human FLK-2.

The soluble form of the FLK-2 is characterized by lacking the transmembrane sequence, by being encoded by about a 1.9 kb cDNA, capable of competing with the surface membrane FLK-2 for ligand and having at least 80% homology with the sequence (SEQ ID NO:3) set forth for Flk-2ws in the Experimental section. Substantial sequence conservation of the gene and protein is observed, so that the soluble form may be from primate, particularly human, murine, bovine, ovine, equine, lagomorpha, feline, canine, etc.

Nucleic acid encoding Flk-2ws may be obtained from host hematopoietic stem cells by using as a probe, at least twelve, usually at least eighteen, nucleotides of the subject sequence. The subject sequence, which is the mouse sequence, may be used to identify other mammalian analogs by hybridizing under less stringent conditions, e.g., (1) 6×SSC, 35° C., 1 hr.; (2) 0.5×SSC, 35° C., 0.5 hr.; (3) 0.5×SSC, 50° C., 1 hr., and using Northern blots, dot-blots, or the like. cDNA's may then be prepared from the mRNA in accordance with known procedures.

The cDNA may be used for expression of the Flk-2ws in any convenient expression host, both prokaryotic and eukaryotic hosts. By forming an expression cassette in the direction of transcription of a transcriptional initiation regulatory region, which may or may not include an enhancer, the cDNA or other sequence encoding the same or substantially the same protein, and a transcriptional termination regulatory region, desirably including a polyadenylation signal sequence, the cassette then may be used for introduction into the appropriate host, where the regulatory regions are functional in the host. A wide variety of both prokaryotic and eukaryotic hosts are available, such as *E. coli, B. subtilis,* yeast, such as *S. cerevisiae,* Kluyveromyces, fungi, such as proteus, etc., insect cells, mammalian cells, e.g., COS cells, CHO cells, etc., plant cells, and the like. The particular choice of the host is not critical to this invention, and any host may be employed which allows for the desired expression and, as appropriate, processing.

For scientific investigation, the subject composition may be labeled for detection. Various labels include radioisotopes, enzymes, fluorescers, and the like. Methods of labeling a protein are well established in the literature, and need not be exemplified here.

The strategy employed for identifying the Flk-2ws was to isolate hematopoietic stem cells by separation using long-term cultured w/w hematopoietic stem cells, where the w/w mice lack a functional c-kit gene, the receptor for the steel ligand. The cultured cells were then used for isolation of mRNA, followed by reverse transcription to provide cDNA. Amplification was then achieved using the polymerase chain reaction (PCR), with primers having homology to the 5' terminal sequence and the sequence 3' of about nucleotide 3400, from about 3400 to about 3430. After separation by 1% agarose gel electrophoresis, two major amplified fragments were cloned, namely a 3.4 and a 1.9 kb DNA fragment. The 3.4 kb DNA fragment represents the native Flk-2 molecule, while the 1.9 kb DNA fragment (SEQUENCE ID NO:3) represents a secreted form of Flk-2, designated Flk-2ws.

For isolation of the human, Flk-2, human fetal bone marrow cells were selected for carrying the markers CD 34$^+$Thy-1$^+$, separation being by any convenient means such as magnetic particles, fluorescence activated cell sorter, panning or the like. Isolated mRNA was used to prepare a cDNA library and mouse Flk-2ws (SEQUENCE ID NO:3), or a major portion thereof, may be used as a probe. Stringent conditions were used, employing elevated temperature in the range of about 50 to 65° C., employing a stringency of about 6×SSC. After cloning in λ phage, positive plaques were selected and re-screened and phagemids rescued from the secondary positive λ phage clones. The clones which were obtained lack the 5' end which was obtained by using a portion of the mouse Flk-2 (SEQUENCE ID NO:6) as a probe. The positive clones were then used to provide the 5' end sequence.

The human Flk-2 is (SEQUENCE ID NO:5) substantially homologous to the mouse Flk-2 (SEQUENCE ID NO:6)

having the sequence as set forth in the experimental section. It is characterized by being 2.5 kbp. It defines domains analogous to the domains for the mouse membrane bound Flk-2 and soluble Flk-2.

The subject protein may be obtained in purified form, usually at least about 90% pure, preferably at least about 99% pure, as evidenced by a single band in gel electrophoresis.

The subject proteins find use in culture and in vivo in competing with Flk-2 receptor for Flk-2 ligand. Thus, the subject compositions may be used for modulating the growth of hematopoietic progenitor cells. In addition, the subject proteins or fragments thereof of at least about 12 amino acids, preferably at least about 18 amino acids, may be used for the production of antibodies, either polyclonal anti-serum or monoclonal antibodies. Particularly, the soluble Flk-2 may be used to produce antibodies which are specific for the juncture or sequences proximal to the juncture between about amino acids 680 and 700, particular at about 690, ±10 amino acids. The antibodies may be used for identifying cells carrying Flk-2, removing soluble Flk-2 from culture fluids or natural fluids, purifying Flk-2, and the like. The antibodies may also be used for assaying for the presence of Flk-2.

The following examples are offered by way of illustration and not be way of limitation.

EXPERIMENTAL

Strategy

Long-term cultured w/w stem cells were used as starting material for mRNA isolation. The isolated RNA was used to make cDNA which was then amplified using the polymerase chain reaction with a pair of mouse Flk-2 specific primers. Two DNA fragments migrating at 3.4 and 1.9 kb were identified as the main PCR products. The two DNA fragments were isolated and cloned, and the DNA sequence of the 3.4 Kb product was identical to the previously reported DNA sequence (Matthews et al. (1991) *Proc. Natl. Acad. Sci. USA* 88, 9026–9030), while the 1.9 kb DNA fragment represented a secreted soluble Flk-2 molecule (SEQUENCE ID NO:3), apparently resulting from RNA editing.

Isolation of Fetal Liver Cells with Stem Cell Phenotype from w/w Mice

Fetal liver cells from newborn w/w mice (Ikuta, K., et al. (1991) *J. Cell Cloning*, 9:451–460) were fractionated into $Lin^+$ $Lin^-$ sub-populations as described previously (Spangrude, G. et al. (1988) *Science* 241:58–62). The $Lin^-$ population of fetal liver cells was further fractionated into Sca-1$^+$, Thy-1$^{+,Lo}$ by FACS. The resulting Sca-1$^+$, Thy-1$^{+,Lo}$ mouse, $Lin^-$ (by FACS) cells were co-cultivated on a monolayer of AC 6.21 (Whitlock, C. et al. (1987) *Cell* 48:1009–1021) stromal cell line for several weeks. Approximate 1–2% of the long-term culture w/w cells still retained the stem cell phenotype (about 80% of long-term cultured fetal liver cells exhibited B220 positive phenotype).

Isolation of mRNA, cDNA Synthesis PCR

Approximately 2×10$^5$ long-term cultured w/w stem cells were collected and used for mRNA isolation. The mRNA was isolated with a Mini-Fast Track in an mRNA isolation kit (Invitrogen). The mRNA (about 25 ng) from w/w stem cells was primed with oligo dT and reverse-transcribed using avian myeloblastosis virus reverse-transcriptase (BLR) (Maniatis, et al. (1982) *Molecular Cloning: A Laboratory Manual*). The synthesized cDNA was purified and dissolved into 20 μl T-buffer (50 mM Tris-HCl pH 8.3, 50 mM KCl, 10 mM MgCl$_2$, 1 mM DDT, 1 mM EDTA, 2 mM dNTP, 0.5 mM spermidine, 4 mM Na pyrophosphate, 20 pmoles (T) primer). 4 μl of purified cDNA were amplified using a pair of nested primers specific for mouse Flk-2: PCLI and PCLII, Perkin-Elmer-Cetus reagents and Perkin-Elmer Thermal Cycler. The primer PCLII is a 24 mer oligonucleotide with the sequence (SEQUENCE ID NO:3) GAGGCCTGGCTACCGCGCGCTCCG, corresponding to mFlk-2 nucleotide positions 1–24, except that at position 2, C was changed to A. The primer PCLI is a 27 mer oligonucleotide with the sequence (SEQUENCE ID NO:2) ATGGATGGAAATAAACTTTCTACTGTA, corresponding to mFlk-2 nucleotide positions 341 to 3428.

The cycle program for the initial amplification was 95° C. for 1.5 min., 55° C. for 1 min., and 70° C. for 2 min. for a total of 35 cycles. 1 μl of the PCL products from the initial amplification was employed for a second round amplification under the same cycler program. The final PCL products were loaded on a 1% agarose gel. There were two major PCR amplified DNA fragments migrating at 3.4 and 1.9 kb.

Molecular Cloning Flk-2ws and DNA Sequencing

The 3.4 and 1.9 kb DNA fragments which were fractions of the 1% TAE agarose gel were isolated dependently by the NaI-glass bead method (Gene Clean, BIO101) then cloned into pCR1000 vector at the HphI site. Restriction mapping was carried out on the individual clones, with both cDNA inserts hybridizing equally well to the $^{32}$P-label oligo primers specific to mFlk-2, indicating a close relationship between the 1.9 kb cDNA and the 3.4 mFlk-2 molecule.

In order to confirm the relationship, both 1.9 and 3.4 kb inserts were sequenced. The cloned cDNA inserts were sequenced by the dideoxy method of Sanger by using double stranded templates sequenase II (USB), α-$^{35}$S[dATP] (Amersham) and series primers as synthesized according to the mFlk-2 DNA sequence. A comparison of the sequences demonstrated that the 3.4 kb cDNA had the identical DNA sequence to the published mFlk-2, and the 1.9 kb cDNA was an alternative spliced form of the mFlk-2 molecule. The difference was a 1.5 kb internal deletion by differential splicing. There is a 511 amino acid deletion beginning with the amino acid 221 Val and ending with the 731 Gln, so that the Lys at 220 is joined to the Ala at 732.

The 1.9 kb cDNA is designated as mFlk-2ws.

The following provides the DNA (SEQUENCE ID NO:3) and amino acid (SEQUENCE ID NO:4) sequence of Flk-2ws.

```
                                              30                                            60
GCG GCC TGG CTA CCG CGC GCT CCG GAG GCC ATG CGG GCC TTG GCG CAG CGC AGC GAC CGG
                                              Met Arg Ala Leu Ala Gln Arg Ser Asp Arg 90                                           120
CGG CTG CTG CTG CTT GTT GTT TTG TCA GTA ATG ATT CTT GAG ACC GTT ACA AAC CAA GAC
Arg Leu Leu Leu Leu Val Val Leu Ser Val Met Ile Leu Glu Thr Val Thr Asn Gln Asp 150                                           180
CTG CCT GTG ATC AAG TGT GTT TTA ATC AGT CAT GAG AAC AAT GGC TCA TCA GCG GGA AAG
Leu Pro Val Ile Lys Cys Val Leu Ile Ser His Glu Asn Asn Gly Ser Ser Ala Gly Lys 210                                           240
CCA TCA TCG TAC CGA ATG GTG CGA GGA TCC CCA GAA GAC CTC CAG TGT ACC CCG AGG CGC
Pro Ser Ser Tyr Arg Met Val Arg Gly Ser Pro Glu Asp Leu Gln Cys Thr Pro Arg Arg 270                                           300
CAG AGT GAA GGG ACG GTA TAT GAA GCG GCC ACC GTG GAG GTG GCC GAG TCT GGG TCC ATC
Gln Ser Glu Gly Thr Val Tyr Glu Ala Ala Thr Val Glu Val Ala Glu Ser Gly Ser Ile 330                                           360
ACC CTG CAA GTG CAG CTC GCC ACC CCA GGG GAC CTT TCC TGC CTC TGG GTC TTT AAG CAC
Thr Leu Gln Val Gln Leu Ala Thr Pro Gly Asp Leu Ser Cys Leu Trp Val Phe Lys His 390                                           420
AGC TCC CTG GGC TGC CAG CCG CAC TTT GAT TTA CAA AAC AGA GGA ATC GTT TCC ATG GCC
Ser Ser Leu Gly Cys Gln Pro His Phe Asp Leu Gln Asn Arg Gly Ile Val Ser Met Ala 450                                           480
ATC TTG AAC GTG ACA GAG ACC CAG GCA GGA GAA TAC CTA CTC CAT ATT CAG AGC GAA CGC
Ile Leu Asn Val Thr Glu Thr Gln Ala Gly Glu Tyr Leu Leu His Ile Gln Ser Glu Arg 510                                           540
GCC AAC TAC ACA GTA CTG TTC ACA GTG AAT GTA AGA GAT ACA CAG CTG TAT GTG CTA AGG
Ala Asn Tyr Thr Val Leu Phe Thr Val Asn Val Arg Asp Thr Gln Leu Tyr Val Leu Arg 570                                           600
AGA CCT TAC TTT AGG AAG ATG GAA AAC CAG GAT GCA CTG CTC TGC ATC TCC GAG GGT GTT
Arg Pro Tyr Phe Arg Lys Met Glu Asn Gln Asp Ala Leu Leu Cys Ile Ser Glu Gly Val 630                                           660
CCG GAG CCC ACT GTG GAG TGG GTG CTC TGC AGC TCC CAC AGG GAA AGC TGT AAA GAA GAA
Pro Glu Pro Thr Val Glu Trp Val Leu Cys Ser Ser His Arg Glu Ser Cys Lys Glu Glu 690                                           720
GGC CCT GCT GTT GTC AGA AAG GAG GAA AAG GCA CAT TCA AAT TCC AGC ATG CCT GGT TCA
Gly Pro Ala Val Val Arg Lys Glu Glu Lys Ala His Ser Asn Ser Ser Met Pro Gly Ser 750                                           780
CGA GAA GTT CAG TTA CAC CCG CCC TTG GAT CAG CTC TCA GGG TTC AAT GGG AAT TCA ATT
Arg Glu Val Gln Leu His Pro Pro Leu Asp Gln Leu Ser Gly Phe Asn Gly Asn Ser Ile 810                                           840
CAT TCT GAA GAT GAG ATT GAA TAT GAA AAC CAG AAG AGG CTG GCA GAA GAA GAG GAG GAA
His Ser Glu Asp Glu Ile Glu Tyr Glu Asn Gln Lys Arg Leu Ala Glu Glu Glu Glu Glu 870                                           900
GAT TTG AAC GTG CTG ACG TTT GAA GAC CTC CTT TGC TTT GCG TAC CAA GTG GCC AAA GGC
Asp Leu Asn Val Leu Thr Phe Glu Asp Leu Leu Cys Phe Ala Tyr Gln Val Ala Lys Gly 930                                           960
ATG GAA TTC CTG CAG TTC AAG TCG TGT GTC CAC AGA GAC CTG GCA GCC AGG AAT GTC TTG
Met Glu Phe Leu Gln Phe Lys Ser Cys Val His Arg Asp Leu Ala Ala Arg Asn Val Leu 990                                          1020
GTC ACC CAC GGG AAG GTG GTG AAG ATC TGT GAC TTT GGA CTG GCC CGA GAC ATC CTG AGC
Val Thr His Gly Lys Val Val Lys Ile Cys Asp Phe Gly Leu Ala Arg Asp Ile Leu Ser 1050                                          1080
GAC TCC AGC TAC GTC GTC AGG GGC AAC GCA CGG CTG CCG GTG AAG TGG ATG CCA CCC GAG
Asp Ser Ser Tyr Val Val Arg Gly Asn Ala Arg Leu Pro Val Lys Trp Met Ala Pro Glu 1110                                          1140
AGC TTA TTT GAA GGG ATC TAC ACA ATC AAG AGT GAC GTC TGG TCC TAC GGC ATC TTG CTC
Ser Leu Phe Glu Gly Ile Tyr Thr Ile Lys Ser Asp Val Trp Ser Tyr Gly Ile Leu Leu 1170                                          1200
TGG GAG ATA TTT TCA CTG GGT GTG AAC CCT TAC CCT GGC ATT CCT GTC GAC GCT AAC TTC
Trp Glu Ile Phe Ser Leu Gly Val Asn Pro Tyr Pro Gly Ile Pro Val Asp Ala Asn Phe
```

-continued

```
                            1230                                          1260
TAT AAA CTG ATT CAG AGT GGA TTT AAA ATG GAG CAG CCA TTC TAT GCC ACA GAA GGG ATA
Tyr Lys Leu Ile Gln Ser Gly Phe Lys Met Glu Gln Pro Phe Tyr Ala Thr Glu Gly Ile 1290                                          1320
TAC TTT GTA ATG CAA TCC TGC TGG GCT TTT GAC TCA AGG AAG CGG CCA TCC TTC CCC AAC
Tyr Phe Val Met Gln Ser Cys Trp Ala Phe Asp Ser Arg Lys Arg Pro Ser Phe Pro Asn 1350                                          1380
CTG ACT TCA TTT TTA GGA TGT CAG CTG GCA GAG GCA GAA GAA GCA TGT ATC AGA ACA TCC
Leu Thr Ser Phe Leu Gly Cys Gln Leu Ala Glu Ala Glu Glu Ala Cys Ile Arg Thr Ser 1410                                          1440
ATC CAT CTA CCA AAA CAG GCG GCC CCT CAG CAG AGA GGC GGG CTC AGA GCC CAG TCG CCA
Ile His Leu Pro Lys Gln Ala Ala Pro Gln Gln Arg Gly Gly Leu Arg Ala Gln Ser Pro 1470                                          1500
CAG CGC CAG GTG AAG ATT CAC AGA GAA AGA AGT TAG CCA GGA GGC CTT GGA CCC CGC CAC
Gln Arg Gln Val Lys Ile His Arg Glu Arg Ser End 1530                                          1560
CCT AGC AGG CTG TAG ACC GCA GAG CCA AGA TTA GCC TCG CCT CTG AGG AAG CGC CCT ACA 1590                                          1620
GCG CGT TGC TTC GCT GGA CTT TTC TCT AGA TGC TGT CTG CCA TTA CTC CAA AGT GAC TTC 1650                                          1680
TAT AAA ATC AAA CCT CTC CTC GCA CAG GCG GGA GAG CCA ATA ATG AGA CTT GTT GGT GAG 1710                                          1740
CCC GCC TAC CCT GGG GGC CTT TCC ACG AGC TTG AGG GGA AAG CCA TGT ATC TGA AAT ATA 1770                                          1800
GTA TAT TCT TGT AAA TAC GTG AAA CAA ACC AAA CCC GTT TTT TGC TAA GGG AAA GCT AAA 1830                                          1860
TAT GAT TTT TAA AAA TCT ATG TTT TAA AAT ACT ATG TAA CTT TTT CAT CTA TTT AGT GAT

1890
ATA TTT TAT GGA TGG AAA TAA ACT TTC TAC TGT A
```

The following provides a partial sequence of the human Flk-2 (SEQUENCE ID NO:5) compared to the mouse sequence (SEQUENCE ID NO:6).

azide. The hybridized filters are washed twice with 6×SSC at room temperature for 10 min., 3 times with 0.5×SSC and 0.1% SSC at room temperature for 10 min.

```
                                          LIMITS:  1483  1628
                                          LIMITS:    10   160

1483    AATAAAAAGGCTAACAGAAAAGTGTTTGGCCAGTGGGTGTCGAGCAGTACTCTAAA
        ||||  ||||||||||||||||||||||||| ||||||||||||||||||||||||
10      CTGGAATAGAAAGGCTAACAGAAAAGTGTTTGGACAGTGGGTGTCGAGCAGTACTCTAAA

1539    TATGAGTGAGGCCGGGAAAGGGCTTCTGGTCAAATGCTGTGCGTACAATTCTATGGGCAC
        |||||||| |||     |||||| ||||||||||| |||||||  |||||||  | |||||
70      CATGAGTGAAGCCATAAAAGGG TTCTGGTCAAGTGCTGTGACTACAATTCCCTTGGCAC

1599    GTCTTGCGAAACCATCTTTTTAAACTC ACC
        || || || | |||| |||||||||||| |||
129     ATC TGTGAGAGCATCCTTTTAAACTCTACCGG

Matches = 126    Mismatches = 18    Unmatched = 9
Length = 153     Matches/length = 82.4 percent
```

Human Flk-2 (hu Flk-2)

Strategy

The mRNA from 3×10[5] Thy-1[+] CD34[+] human fetal bone marrow cells is used to construct a cDNA library in Uni-Zip λ (Strategene). Approximately 10[5] phage plaques from the cDNA library are transferred onto nitrocellulose filters and are screened with $^{32}$P-labeled full length mFlk-2ws as a probe. The hybridization condition is 60° C., 12 hours in 6×SSC 0.5% dry milk, 1 mM EDTA and 0.02% sodium azide. The hybridized filters are washed twice with 6×SSC at room temperature for 10 min., 3 times with 0.5×SSC and 0.1% SSC at room temperature for 10 min.

Positive plaques are picked and re-screened with $^{32}$P-labeled mFlk-2ws probe. Phagemids are rescued from the secondary positive λ phage clones, the cDNA inserts evaluated by Southern blots with the same probe as above. The cDNA inserts are then screened for size and partial DNA sequences taken to establish their relationship to the mFlk-2ws.

It is evident from the above results, that a novel soluble form of Flk-2 is provided, which finds use in investigating hematopoiesis, competing with the surface membrane bound Flk-2 for ligand, producing antibodies for assaying for the presence of Flk-2, either on the surface of cells or in a medium, and in culture and in therapy in association with the modulation of hematopoiesis. Also, the human surface membrane bound Flk-2 may be used in analogous ways and may further be used employing recombinant techniques to fuse various domains of Flk-2 to domains of other proteins to provide novel fused proteins for novel properties associated with the two domains.

What is claimed is:

1. A cDNA sequence (SEQUENCE ID NO:3) encoding soluble Flk-2.

2. An expression cassette comprising a cDNA sequence (SEQUENCE ID NO:3) encoding soluble Flk-2 joined to and under the regulation of a transcriptional and translational regulatory region.

3. A vector comprising the expression cassette according to claim 2.

4. A method of producing soluble Flk-2, said method comprising:

growing a cell comprising an expression cassette according to claim 2, wherein said regulatory region is functional in said cell;

recovering soluble Flk-2 from a culture of said cells;

whereby soluble Flk-2 is expressed.

5. Soluble Flk-2 (SEQUENCE ID NO:4) as a purified composition.

* * * * *